United States Patent
Frutos et al.

(10) Patent No.: US 7,981,665 B2
(45) Date of Patent: Jul. 19, 2011

(54) SUPPORTS FOR ASSAYING ANALYTES AND METHODS OF MAKING AND USING THEREOF

(75) Inventors: Anthony G. Frutos, Painted Post, NY (US); David Henry, Morigny-Champigny (FR)

(73) Assignee: Corning Incorporated, Corning, NY (US)

( * ) Notice: Subject to any disclaimer, the term of this patent is extended or adjusted under 35 U.S.C. 154(b) by 319 days.

(21) Appl. No.: 12/357,872

(22) Filed: Jan. 22, 2009

(65) Prior Publication Data

US 2009/0137425 A1 May 28, 2009

Related U.S. Application Data

(62) Division of application No. 11/448,486, filed on Jun. 7, 2006, now Pat. No. 7,781,203.

(60) Provisional application No. 60/754,747, filed on Dec. 29, 2005.

(51) Int. Cl.
C12M 1/34 (2006.01)
G01N 33/544 (2006.01)
G01N 33/547 (2006.01)
C07K 1/10 (2006.01)

(52) U.S. Cl. ............ 435/287.2; 436/528; 436/532; 530/402

(58) Field of Classification Search ............ None
See application file for complete search history.

(56) References Cited

U.S. PATENT DOCUMENTS

| | | | |
|---|---|---|---|
| 4,407,975 A | 10/1983 | Yamaguchi | 521/27 |
| 4,610,962 A | 9/1986 | Takagi et al. | 435/179 |
| 4,815,843 A | 3/1989 | Tiefenthaler et al. | 356/128 |
| 4,992,385 A | 2/1991 | Godfrey | 436/525 |
| 5,436,161 A | 7/1995 | Bergström et al. | 435/291 |
| 5,624,711 A | 4/1997 | Sundberg et al. | 427/261 |
| 5,629,213 A | 5/1997 | Kornguth et al. | 436/518 |
| 5,858,653 A | 1/1999 | Duran et al. | 435/6 |
| 6,528,264 B1 | 3/2003 | Pal et al. | 435/6 |
| 6,541,071 B1 | 4/2003 | Bookbinder et al. | 427/407.2 |
| 6,632,615 B2 | 10/2003 | Mallet et al. | 435/7.1 |
| 6,884,628 B2 | 4/2005 | Hubbell et al. | 436/518 |
| 2002/0127565 A1 | 9/2002 | Cunningham et al. | 435/6 |
| 2002/0128234 A1 | 9/2002 | Hubbell et al. | 514/100 |
| 2002/0168295 A1 | 11/2002 | Cunningham et al. | 422/82.05 |
| 2003/0017464 A1 | 1/2003 | Pohl | 435/6 |
| 2003/0017580 A1 | 1/2003 | Cunningham et al. | 435/287.2 |
| 2003/0017581 A1 | 1/2003 | Li et al. | 435/287.2 |
| 2003/0026891 A1 | 2/2003 | Qiu et al. | 427/58 |
| 2003/0027327 A1 | 2/2003 | Cunningham et al. | 435/287.2 |
| 2003/0027328 A1 | 2/2003 | Cunningham et al. | 435/287.2 |
| 2003/0032039 A1 | 2/2003 | Cunningham et al. | 435/6 |
| 2003/0059855 A1 | 3/2003 | Cunningham et al. | 435/7.9 |

(Continued)

FOREIGN PATENT DOCUMENTS

JP 05-271299 10/1993

(Continued)

OTHER PUBLICATIONS

C.T. Chang et al., "Effects of Microscopic and Macroscopic Viscosity on the Rate of Renaturation of DNA", Biopolymers, 1974, vol. 13, pp. 1847-1858.

(Continued)

Primary Examiner — Shafiqul Haq
(74) Attorney, Agent, or Firm — John L. Haack

(57) ABSTRACT

Described herein are supports for assaying an analyte and methods of making and using thereof.

22 Claims, 13 Drawing Sheets

U.S. PATENT DOCUMENTS

| | | | |
|---|---|---|---|
| 2003/0068657 A1 | 4/2003 | Lin et al. | 435/7.9 |
| 2003/0077660 A1 | 4/2003 | Pien et al. | 435/7.1 |
| 2003/0092075 A1 | 5/2003 | Pepper | 435/7.9 |
| 2003/0113766 A1 | 6/2003 | Pepper et al. | 435/6 |
| 2004/0043497 A1 | 3/2004 | Feuer et al. | 436/86 |
| 2004/0043508 A1 | 3/2004 | Frutos et al. | 436/518 |
| 2004/0062854 A1 | 4/2004 | Jan et al. | 427/2.11 |
| 2004/0091602 A1 | 5/2004 | Hwang et al. | 427/2.11 |
| 2004/0132172 A1 | 7/2004 | Cunningham et al. | 435/287.2 |
| 2004/0132214 A1 | 7/2004 | Lin et al. | 436/518 |
| 2004/0151626 A1 | 8/2004 | Cunningham et al. | 422/58 |
| 2004/0223881 A1 | 11/2004 | Cunningham et al. | 422/82.05 |
| 2006/0110594 A1 | 5/2006 | Frutos et al. | 428/332 |

FOREIGN PATENT DOCUMENTS

| | | |
|---|---|---|
| JP | 10-234847 | 9/1998 |
| WO | WO 86/02920 | 5/1986 |
| WO | WO 87/06702 | 11/1987 |
| WO | WO 2006/058237 | 6/2006 |

OTHER PUBLICATIONS

J.L. DeRisi et al., "Exploring the Metabolic and Genetic Control of Gene Expression on a Genomic Scale", Science, Oct. 24, 1997, vol. 278, pp. 680-686.

R.T. Gill et al., "Genome-wide Screening for Trait Conferring Genes Using DNA Microarrays", PNAS, May 14, 2002, vol. 99, No. 10, pp. 7033-7038.

P. Hegde et at., "A Concise Guide to cDNA Microarray Analysis", BioTechniques, 2000, vol. 29, No. 3, pp. 548-562.

T.B. Kepler et at, "Normalization and Analysis of DNA Microarray Data by Self-Consistency and Local Regression", Genome Biology, vol. 3. No. 7, pp. 1-12, 2002.

O. Monni et al, "Comprehensive Copy Number and Gene Expression Profiting of the 17q23 Amplicon in Human Breast Cancer", PNAS, May 8, 2001, vol. 98, No. 10, pp. 5711-5716.

G. Li et al., "High Resolution Analysis of DNA Copy-Number Variations in the Human Genome with Oligonucleotide Microarrays", Applied Genomics and Proteomics, 2003, vol. 2, No. 2, pp. 93-100.

N. Faucheux et al., "Self-assembled monolayers with different terminating groups as model substrates for cell adhesion studies", Biomaterials, vol. 25, No. 14, Jun. 2004, pp. 2721-2730.

U. Freudenberg et al., "Covalent Immobilization of Cellulose Layers onto Maleic Anhydride Copolymer Thin Films", Biomacromolecules, 2005, vol. 6, No. 3, pp. 1628-1634.

W. Pan et al, "How Many Replicates of Arrays are Required to Detect Gene Expression Changes in Microarray Experiments? A Mixture Model Approach", Genome Biology, vol. 3, No. 5, pp. 1-10, 2002.

D. Beyer et al., "Surface Modification Via Reactive Polymer Interlayers", Langmuir, 1996, vol. 12, pp. 2514-2518.

J Rao et al., "Using Surface Plasmon Resonance to Study the Binding of Vancomycin and Its Dimer to Self-Assembled Monolayers Presenting D-Ala-D-Ala", J. Am. Chem. Soc., 1999, vol. 121, pp. 2629-2630.

E. Ostuni et al., "A Survey of Structure—Property Relationships of Surfaces that Resist the Adsorption of Protein", Langmuir, 2001, vol. 17, pp. 5605-5620.

A. Frostell-Karlsson et al., "Biosensor Analysis of the Interaction between Immobilized Human Serum Albumin and Drug Compounds for Prediction of Human Serum Albumin Binding Levels", J. Med. Chem., 2000, vol. 43, pp. 1986-1992.

D. Beyer et al., "Thin Polymer Layers as Supports for Hippocampal Cell Cultures", Langmuir, 1998, vol. 14, pp. 3030-3035.

S.A. Evenson et al, "Surface Esterification of Poly(Ethylene-*alt*-Maleic Anhydride) Copolymer", J. Phys. Chem. B., 2000, vol. 104, pp. 10608-10611.

S.A. Evenson et al, "Solventless Attachment of Long-Chain Molecules to Poly(ethylene-*alt*-maleic anhydride) Copolymer Surfaces", J. Phys. Chem. B, 1998, vol. 102, pp. 5500-5502.

C. Ladavière et al., "Electrostatically Driven Immobilization of Peptides onto (Maleic Anhydride-*alt*-methyl Vinyl Ether) Copolymers in Aqueous Media", Bioconjugate Chem., 2000, vol. 11, pp. 146-152.

C. Ladavière et al., "Reactive Polymers in Diagnostics: Syntheses and Characterizations of Nucleic Acid Probes and Maleic Anhydride-*co*-Methyl Vinyl Ether Polymers", Journal of Applied Polymer Science, 1997, vol. 65, pp. 2567-2577.

A. Satoh et al., "Comparison of Methods of Immobilization to Enzyme-Linked Immunosorbent Assay Plates for the Detection of Sugar Chains", Analytical Biochemistry, 1999, vol. 275, pp. 231-235.

S.A. Evenson et al., "Controlled Monomolecular Functionalization and Adhesion of Solid Surfaces", Chem. Mater., 2000, vol. 12, pp. 3038-3043.

C. Chaix et al., "Oligonucleotide Synthesis on Maleic Anhydride Copolymers Covalently Bound to Silica Spherical Support and Characterization of the Obtained Conjugates", Journal of Applied Polymer Science, 1998, vol. 70, pp. 2487-2497.

C. Minard-Basquin et al., "Oligonucleotide-Polymer Conjugates: Effect of the Method of Synthesis on Their Structure and Performance in Diagnostic Assays", Bioconjugate Chem., 2000, vol. 11, pp. 795-804.

C. Ladaviere et al., "Covalent Immobilization of Biological Molecules to Maleic Anhydride and Methyl Vinyl Ether Copolymers—A Physico-Chemical Approach", Journal of Applied Polymer Science, 1999, vol. 71, pp. 927-936.

C Ladavière et al., "Covalent Immobilization of Proteins onto (Maleic Anhydride-*alt*-methyl Vinyl Ether) Copolymers: Enhanced Immobilization of Recombinant Proteins", Bioconjugate Chem., 1998, vol, 9, pp. 655-661.

T. Pompe at al., "Maleic Anhydride Copolymers—A Versatile Platform for Molecular Biosurface Engineering", Biomacromolecules, 2003, vol. 4, pp. 1072-1079.

U. Schmidt et al., "Modification of Poly(octadecene-*alt*-maleic anhydride) Films by Reaction with Functional Amines", Journal of Applied Polymer Science, 2003, vol. 87, pp. 1255-1266.

C. Sperling et al., "Covalently immobilized thrombomodulin inhibits coagulation and complement activation of artificial surfaces in vitro", Biomaterials, 2004, vol. 25, pp. 5101-5113.

L. Eberson et al., "Studies on Cyclic Anhydrides", Acta Chemica Scandinavica, 1972, vol. 26, pp. 239-249.

C. Horvath, "Pellicular Immobilized Enzymes", Biochimica et Biophysica Acta, 1974, vol. 358, pp. 164-177.

S. Löfås et al., "A Novel Hydrogel Matrix on Gold Surfaces in Surface Plasmon Resonance Sensors for Fast and Efficient Covalent lmmoblization of Ligands", J. Chem. Soc., Chem. Commun., 1990, pp. 1526-1528.

A. Relógio et al., "Optimization of Oligonucleotide-Based DNA Microarrays", Nucleic Acids Research, 2002, vol. 30, No. 11 e51, pp. 1-10.

G.M. Wahl et al., "Efficient Transfer of Large DNA Fragments from Agarose Gels to Diazobenzyloxymethyl-Paper and Rapid Hybridization by Using Dextran Sulfate", Proc. Natl. Acad. Sci., USA, Aug. 1979, vol. 76, No. 8, pp. 3683-3687.

H. Yue et al., "An Evaluation of the Performance of cDNA Microarrays for Detecting Changes in Global mRNA Expression", Nucleic Acids Research, 2001, vol. 29, No. 8 e41, pp. 1-9.

J. Lahiri et al., "A Strategy for the Generation of Surfaces Presenting Ligands for Studies of Binding Based on an Active Ester as a Common Reactive Intermediate: A Surface Plasmon Resonance Study", Anal. Chem. 1999, vol. 71, pp. 777-790.

G. Elender et al., "Functionalisation of Si/SiO$_2$ and Glass Surfaces with Ultrathin Dextran Films and Deposition of Lipid Bilayers", Biosensors & Bioelectronics, 1996, vol. 11, No. 6/7, pp. 565-577.

A. Akkoyun et al., "Optimisation of Glass Surfaces for Optical Immunosensors", Biosensors & Bioelectronics, 2002, vol. 17, pp. 655-664.

J.F. Masson et al., "Preparation of Analyte-Sensitive Polymeric Supports for Biochemical Sensors", Talanta, 2004, vol. 64, pp. 716-725.

K. Isosaki et al., "Immobilization of Protein Ligands with Methyl Vinyl Ether-Maleic Anhydride Copolymer", Journal of Chromatography, 1992, vol. 597, pp. 123-128.

B. Johnsson et al., "Immobilization of Proteins to a Carboxymethyldextran-Modified Gold Surface for Biospecific Interaction Analysis in Surface Plasmon Resonance Sensors", Analytical Biochemistry, 1991, vol. 198, pp. 268-277.

A. Satoh et al., "Immobilization of Saccharides and Peptides on 96-Well Microtiter Plates Coated with Methyl Vinyl Ether-Maleic Anhydride Copolymer", Analytical Biochemistry, 1998, vol. 260, pp. 96-102.

F. Zhang et al., "Mechanochemical Preparation and Properties of a Cellulose-Polyethylene Composite", J. Mater. Chem., 2002, vol. 12, pp. 24-26.

G.T. Hermanson, "Bioconjugate Techniques", Academic Press, ISBN 0-12-342336-8, Section 1.12 Anhydrides, pp. 145-146, 1996.

T.K. Jenssen et al., "Analysis of Repeatability in Spotted cDNA Microarrays", Nucleic Acids Research, 2002, vol. 30, No. 14, pp. 3235-3244.

G.T. Hermanson et al., "Immobilized Affinity Ligand Techniques", Academic Press, ISBN 0-12-342330-9, Section 3.1.1.8 Blocking or Capping Agents, pp. 156-157, 1992.

R. Polzius et al., "Optimization of Biosensing Using Grating Couplers: Immobilization on Tantalum Oxide Waveguides", Biosensors & Bioelectronics, 1996, vol. 11, No. 5, pp. 503-514.

SUPPORTS FOR ASSAYING ANALYTES AND METHODS OF MAKING AND USING THEREOF

CROSS-REFERENCE TO RELATED APPLICATIONS

This application is a divisional of, and claims the benefit of priority to U.S. patent application Ser. No. 11/448,486, filed on Jun. 7, 2006 now U.S. Pat. No. 7,781,203, which claims the benefit of U.S. Application Ser. No. 60/754,747 filed on Dec. 29, 2005 and entitled "Supports for Assaying Analytes and Methods of Making and Using Thereof" which is incorporated by reference herein in.

BACKGROUND

Assays using label independent detection (LID) platforms (e.g. surface plasmon resonance (SPR) or resonant waveguide grating sensors) are typically performed using a two step procedure: (i) immobilization of one of the binding partners (e.g., a protein) on the surface of the sensor; and (ii) binding of a ligand (e.g., drug, protein, oligonucleotide, etc) to the immobilized protein. Traditionally, the coupling of biomolecules to surfaces involves the activation of carboxylic acid groups on the surface to reactive N-hydroxysuccinimide (NHS) esters, which are then coupled to amino groups on the protein of interest. This method has been successfully used and commercialized by Biacore, Affinity Biosensors, and Artificial Sensing Instruments for their respective LID platforms. While effective, the activation step is time consuming and involves the handling and use of somewhat toxic chemicals.

An alternative to this approach involves the use of "preactivated" chemistries. For example, surfaces presenting aldehyde groups have been used to bind biomolecules. However, a reduction step is required after coupling to stabilize the resulting Schiff base. Surfaces with epoxide and isocyanate functionalities have also been used; however, the epoxide group is relatively slow to react and, therefore, requires long incubation times under very basic conditions, while the isocyanate group is extremely reactive and presents storage stability issues. Because of these issues, there are few reports of the use of preactivated chemistries for LID platforms. In fact, neither Biacore, Affinity Biosensors, nor ASI—the three companies offering the most popular LID platforms—offer sensors with a preactivated chemistry.

Maleic anhydride reacts readily with nucleophiles such as amino groups. Although the modification of surfaces with maleic anhydride copolymer layers for the immobilization of small molecules, DNA, sugars, and peptides has been described, the hydrolytic stability of maleic anhydrides is rather poor, and for this reason they have not been widely used. The hydrolytic stability of maleic anhydride can be increased when copolymerized with hydrophobic side chains (e.g. styrene); however, this leads to problems with nonspecific binding of biomolecules to the surface. While this may be an advantage for some applications such as mass spectrometry, it is problematic for LID.

There is a unique issue with LID detection in general that necessitates a stringent requirement for biospecificity. The incorporation of "blocking agents" (e.g. bovine serum albumin, BSA) in the analyte solution is undesirable because both specific (due to the analyte) and non-specific (due to the blocking agent) binding would contribute to changes in interfacial refractive index and would hence be indistinguishable. This problem is only exacerbated when complex samples are used or when the analyte is impure. The concern with anhydrides for immobilization of biomolecules such as, for example, proteins is non-specific binding due to the formation of residual negative charge and the influence of other groups (e.g. styrene, ethylene, methyl vinyl ether, etc) in the polymer. Because of these reasons, the feasibility of using anhydride polymers for LID is a potential concern.

The supports and methods described herein provide numerous advantages. For example, the support does not need to be activated, which saves the user time, cost, and complexity. The supports and methods described herein permit the loading of high amounts of biomolecules, which leads to better sensitivity with respect to detecting an analyte. Additionally, the methods for producing the supports permit high-volume manufacturing of the supports. In general, the supports are stable and can be stored for extended (~6 months) periods of time with little or no loss in binding capacity. Moreover the coated substrates are slow to hydrolyze under acidic conditions, which permits the binding of various biomolecules under conditions that have not been described using prior art techniques for polymers such as, for example anhydride polymers. Finally, the supports and methods also increase array signal intensity, sensitivity and assay quality in a timely and economical manner and further improve the assay specificity.

SUMMARY

Described herein are supports for assaying analytes and methods of making and using thereof. The advantages of the materials, methods, and articles described herein will be set forth in part in the description which follows, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below. It will be appreciated that these drawings depict only typical embodiments of the materials, articles, and methods described herein and are therefore not to be considered limiting of their scope.

DETAILED DESCRIPTION

Figure 1:
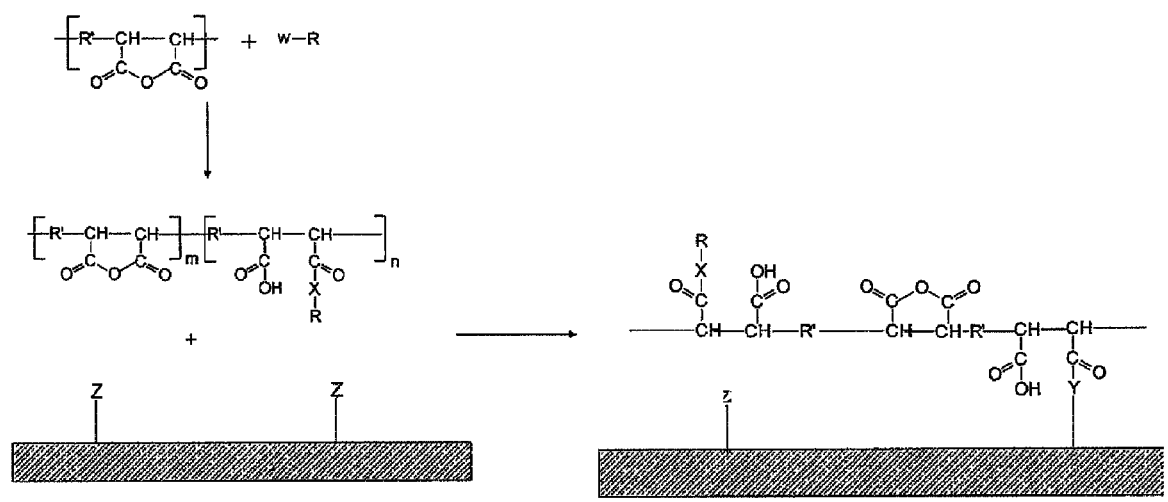
FIG. 1 shows a schematic representation of the pre-blocking step and attachment of the pre-blocking maleic anhydride based polymer onto the support.

Before the present materials, articles, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed, then "less than or equal to 10" as well as "greater than or equal to 10" is also disclosed. It is also understood that throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

By "contacting" is meant an instance of exposure by close physical contact of at least one substance to another substance.

The term "attached" as used herein is any chemical interaction between two components or compounds. The type of chemical interaction that can be formed will vary depending upon the starting materials that are selected and reaction conditions. Examples of attachments described herein include, but are not limited to, covalent, electrostatic, ionic, hydrogen, or hydrophobic bonding.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a number of different polymers and biomolecules are disclosed and discussed, each and every combination and permutation of the polymer and biomolecule are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-B, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, B, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

I. Supports and Methods of Making Thereof

Described herein are supports useful for performing assays. In one aspect, described herein is a support for performing an assay, comprising a substrate and a binding polymer directly or indirectly attached to the substrate, wherein the binding polymer has a plurality of reactive groups capable of attaching to a biomolecule and a plurality of ionizable groups, wherein the ratio of reactive groups to ionizable groups is from 0.5 to 10, wherein the binding polymer does not contain a photoreactive group.

Also described herein are methods for making a support for performing an assay, comprising attaching a binding polymer directly or indirectly attached to a substrate, wherein the binding polymer has a plurality of reactive groups capable of attaching to a biomolecule and a plurality of ionizable groups, wherein the ratio of reactive groups to ionizable groups is from 0.5 to 10.0, wherein the binding polymer does not contain a photoreactive group.

In another aspect, described herein are methods for making a support for performing an assay, comprising a. attaching a binding polymer directly or indirectly attached to a substrate, wherein the binding polymer has a plurality of reactive groups capable of attaching to a biomolecule, wherein the binding polymer does not contain a photoreactive group, and b. converting the reactive groups to ionizable groups so that the ratio of reactive groups to ionizable groups is from 0.5 to 10.0.

a. Substrates

The substrates that can be used herein include, but are not limited to, a microplate, a slide, or any other material that is capable of attaching to the binding polymer. In one aspect, when the substrate is a microplate, the number of wells and well volume will vary depending upon the scale and scope of the analysis. Other examples of substrates useful herein include, but are not limited to, a cell culture surface such as a 384-well microplate, a 96-well microplate, 24-well dish, 8-well dish, 10 cm dish, or a T75 flask.

For optical or electrical detection applications, the substrate can be transparent, impermeable, or reflecting, as well as electrically conducting, semiconducting, or insulating. For biological applications, the substrate material can be either porous or nonporous and can be selected from either organic or inorganic materials.

In a further aspect, the substrate comprises a plastic, a polymeric or co-polymeric substance, a ceramic, a glass, a metal, a crystalline material, a noble or semi-noble metal, a metallic or non-metallic oxide, an inorganic oxide, an inorganic nitride, a transition metal, or any combination thereof. Additionally, the substrate can be configured so that it can be placed in any detection device. In one aspect, sensors can be integrated into the bottom/underside of the substrate and used for subsequent detection. These sensors could include, but are not limited to, optical gratings, prisms, electrodes, and quartz crystal microbalances. Detection methods could include fluorescence, phosphorescence, chemiluminescence, refractive index, mass, electrochemical. In one aspect, the substrate is a resonant waveguide grating sensor.

In a further aspect, the substrate can be composed of an inorganic material. Examples of inorganic substrate materials include, but are not limited to, metals, semiconductor materials, glass, and ceramic materials. Examples of metals that can be used as substrate materials include, but are not limited to, gold, platinum, nickel, palladium, aluminum, chromium, steel, and gallium arsenide. Semiconductor materials used for the substrate material include, but are not limited to, silicon and germanium. Glass and ceramic materials used for the substrate material can include, but are not limited to, quartz, glass, porcelain, alkaline earth aluminoborosilicate glass and other mixed oxides. Further examples of inorganic substrate materials include graphite, zinc selenide, mica, silica, lithium niobate, and inorganic single crystal materials. In another aspect, the substrate can be made of gold such as, for example, a gold sensor chip.

In a further aspect, the substrate comprises a porous, inorganic layer. Any of the porous substrates and methods of making such substrates disclosed in U.S. Pat. No. 6,750,023, which is incorporated by reference in its entirety, can be used herein. In one aspect, the inorganic layer on the substrate comprises a glass or metal oxide. In another aspect, the inorganic layer comprises a silicate, an aluminosilicate, a boroaluminosilicate, a borosilicate glass, or a combination thereof. In a further aspect, the inorganic layer comprises $TiO_2$, $SiO_2$, $Al_2O_3$, $Cr_2O_3$, $CuO$, $ZnO$, $Ta_2O_5$, $Nb_2O_5$, $ZnO_2$, or a combination thereof. In another aspect, the substrate comprises $SiO_2$ with a layer comprising $Ta_2O_5$, $Nb_2O_5$, $TiO_2$, $Al_2O_3$, silicon nitride or a mixture thereof, wherein the layer is adjacent to the surface of the $SiO_2$. The silicon nitride can be represented by the formula $SiN_x$, where the stoichiometry of silicon and nitrogen can vary.

In a further aspect, the substrate can be composed of an organic material. Organic materials useful herein can be made from polymeric materials due to their dimensional stability and resistance to solvents. Examples of organic substrate materials include, but are not limited to, polyesters, such as polyethylene terephthalate and polybutylene terephthalate; polyvinylchloride; polyvinylidene fluoride; polytetrafluoroethylene; polycarbonate; polyamide; poly(meth)acrylate; polystyrene, polyethylene; or ethylene/vinyl acetate copolymer.

In a further aspect, the substrate can be composed of a material that possesses groups capable of attaching one or more biomolecules. For example, the substrate can be composed of one or more binding polymers described herein and molded into any desired shape. In this aspect, the biomolecule and other components can be attached directly to the substrate.

b. Binding Polymer

In various aspects, a binding polymer comprising one or more reactive groups that can bind a biomolecule to the substrate can be directly or indirectly attached to the substrate. The "reactive group" on the binding polymer permits the attachment of the binding polymer to the biomolecule. The reactive groups can also facilitate the attachment of the binding polymer to the substrate. In a further aspect, the binding polymer can be covalently and/or electrostatically attached to the substrate. The binding polymer can have one or more different reactive groups. It is also contemplated that two or more different binding polymers can be attached to the substrate.

In various aspects, the reactive group is capable of forming a covalent bond with a nucleophile such as, for example, an amine or thiol. The amine or thiol can be derived from the biomolecule or a molecule that is attached to the surface of the substrate (i.e., a tie layer) and used to indirectly attach the binding polymer to the substrate. Examples of reactive groups include, but are not limited to, an anhydride group, an epoxy group, an aldehyde group, an activated ester (e.g., n-hydroxysuccinimide (NHS), which is an ester with a leaving group), an isocyanate, an isothiocyanate, a sulfonyl chloride, a carbonate, an aryl or alkyl halide, an aziridine, or a maleimide. It is contemplated that two or more different reactive groups can be present on the binding polymer.

Also present on the binding polymer is a plurality of ionizable groups. Ionizable groups as defined herein are groups that can be converted to a charged (i.e., ionic) group under particular reaction conditions. For example, a carboxylic acid (an ionizable group) can be converted to the corresponding carboxylate (charged group) by treating the acid with a base. The charged groups can be either positive or negative. An example of a positively charged group is an ammonium group. Examples of negatively charged groups include carboxylate, sulfonate, and phosphonate groups. It is contemplated that two or more different ionizable groups can be present on the binding polymer.

The binding polymer can be water-soluble or water-insoluble depending upon the technique used to attach the binding polymer to the substrate. The binding polymer can be either linear or non-linear. For example, when the binding polymer is non-linear, the binding polymer can be branched, hyperbranched, crosslinked, or dendritic polymer. The binding polymer can be a homopolymer or a copolymer.

In one aspect, the binding polymer comprises a copolymer derived from maleic anhydride and a first monomer. In this aspect, the amount of maleic anhydride in the binding polymer is from 5% to 50%, 5% to 45%, 5% to 40%, 5% to 35%, 5% to 30%, 5% to 25%, 10% to 50%, 15% to 50%, 20% to 50%, 25% to 50%, or 30% to 50% by stoichiometry (i.e., molar amount) of the first monomer. In one aspect, the first monomer selected improves the stability of the maleic anhydride group in the binding polymer. In another aspect, the first monomer reduces nonspecific binding of the biomolecule to the substrate. In a further aspect, the amount of maleic anhydride in the binding polymer is about 50% by stoichiometry of the first monomer. In another aspect, the first monomer comprises styrene, tetradecene, octadecene, methyl vinyl ether, triethylene glycol methyl vinyl ether, butylvinyl ether, divinylbenzene, ethylene, dimethylacrylamide, vinyl pyrolidone, a polymerizable oligo(ethylene glycol) or oligo(ethylene oxide), propylene, isobutylene, vinyl acetate, methacrylate, acrylate, acrylamide, methacrylamide, or a combination thereof.

In one aspect, the binding polymer comprises, poly(vinyl acetate-maleic anhydride), poly(styrene-co-maleic anhydride), poly(isobutylene-alt-maleic anhydride), poly(maleic anhydride-alt-1-octadecene), poly(maleic anhydride-alt-1-tetradecene), poly(maleic anhydride-alt-methyl vinyl ether), poly(triethyleneglycol methylvinyl ether-co-maleic anhydride), poly(ethylene-alt-maleic anhydride), or a combination thereof.

The binding polymers useful herein do not contain a photoreactive group. Photoreactive groups respond to specific applied external stimuli to undergo active species generation with resultant covalent bonding to an adjacent chemical structure, e.g., as provided by the same or a different molecule. Photoreactive groups are those groups of atoms in a molecule that retain their covalent bonds unchanged under conditions of storage; however, upon activation by an external energy source, form covalent bonds with other molecules. The photoreactive groups generate active species such as free radicals and particularly nitrenes, carbenes, and excited states of ketones upon absorption of electromagnetic energy.

c. Ratio of Reactive Groups to Ionizable Groups

In one aspect, the ratio of reactive groups to ionizable groups is from 0.5 to 5.0. In other aspects, the lower endpoint of the ratio is 0.5, 0.6, 0.7, 0.8, 0.9, 1.0, 1.5, 2.0, 2.5, 3.0, 3.5, 4.0, 4.5, or 5.0 and the upper endpoint is 2.0, 2.5, 3.0, 3.5, 4.0, 4.5, 5.0, 5.5, 6.0, 6.5, 7.0, 7.5, 8.0, 8.5, 9.0, 9.5, or 10.0, where any lower and upper endpoint can form the ratio range. In another aspect, the ratio of reactive groups to ionizable groups is from 0.5 to 9.0, 0.5 to 8.0, 0.5 to 7.0, 0.5 to 6.0, 0.5 to 5.0, 0.5 to 4.0, 0.5 to 3.0, 0.6 to 3.0, 0.65 to 3.0, or 0.67 to 3.0.

The formation and number of reactive groups and ionizable groups present on the binding polymer can be controlled in a number of ways. In one aspect, the binding polymer can be synthesized from monomers possessing reactive groups and monomers with ionizable groups. In this aspect, the stoichiometry of the monomers selected can control the ratio of reactive groups and ionizable groups. In another aspect, a polymer possessing just reactive groups can be treated so that some of the reactive groups are converted to ionizable groups prior to attaching the binding polymer to the substrate. The starting polymer can be commercially available or synthesized using techniques known in the art. In another aspect, a polymer can be attached to the substrate, and the attached polymer can be treated with various reagents to add either reactive groups and ionizable groups or convert reactive groups to ionizable groups. In another aspect, the binding polymer that possesses reactive groups can be attached to the substrate, where the substrate reacts with the reactive groups and produces ionizable groups.

For example, referring to FIG. 1, when a polymer with a repeat unit of R'-maleic anhydride, where R' can be a residue of an unsaturated monomer selected among monomers able to copolymerize with maleic anhydride such as, for example, ethylene, propylene, isobutylene, octadecene, tetradecene, vinyl acetate, styrene, vinyl ethers such as methyl vinyl ether, butyl vinyl ether, triethylene glycol vinylether, (meth)acrylates, (meth)acrylamide, vinyl pyrrolidinone, polymerizable oligo(ethylene glycol) or oligo(ethylene oxide) is reacted with W—R, where W is a nucleophilic group such as, for example, $NH_2$, OH, or SH and R can be hydrogen or a substituted or unsubstituted alkyl group (linear or branched) having less than 6, an oligo(ethylene oxide) or oligo(ethylene glycol), or a dialkyl amine such as dimethyl amino propyl or diethyl amino propyl, the anhydride ring-opens and produces the carboxylic acid (an ionizable group). This step is referred to as preblocking. The pre-blocked polymer can then be applied to the surface of the substrate. Referring to FIG. 1, if the substrate possesses nucleophilic groups Z, where Z can be for example $NH_2$, OH, or SH, these groups can react with the maleic anhydride groups present on the pre-blocked polymer to form a covalent bond between the pre-blocked polymer and the substrate.

The ratio of reactive groups to ionizable groups can be controlled by using specific amounts of reagents. Other properties of the binding polymer (e.g., hydrophobicity) can be altered as needed by controlling the starting materials used to prepare the binding polymer (e.g., selection of hydrophobic monomers) or by appropriate choice of the derivatizing/blocking reagent. In certain aspects, the ratio of reactive groups to ionizable groups can be controlled by converting the one or more reactive groups to inactive groups. In a further aspect, from about 10% to about 50% of the reactive groups present on the binding polymer are blocked or rendered inactive. The term "blocked" as used herein is the conversion of a reactive group present on the binding polymer to an inactive group, where the inactive group does not form a covalent attachment with a biomolecule. In various aspects, the amount of reactive groups that are blocked is about 10%, about 12%, about 14%, about 16%, about 18%, about 20%, about 22%, about 24%, about 26%, about 28%, about 30%, about 32%, about 34%, about 36%, about 38%, about 40%, about 42%, about 44%, about 46%, about 48%, or about 50%, where any value can form a lower and upper endpoint of a range. In a further aspect, from about 10% to about 45%, 10% to about 40%, 10% to about 35%, 15% to about 35%, 20% to about 35%, or about 25% to about 35% of the reactive groups are blocked.

It is contemplated that the blocking agent can react with the binding polymer prior to attaching the binding polymer to the substrate or, in the alternative, the binding polymer can be attached to the substrate first followed by blocking with the blocking agent. In a further aspect, the blocking agent comprises at least one nucleophilic group, the binding polymer comprises at least one electrophilic group, and the blocking agent is attached to the binding polymer by a reaction between the electrophilic group and the nucleophilic group.

In a further aspect, the blocking agent is covalently attached to the binding polymer. For example, when the blocking agent comprises an amine group, hydroxyl group, or thiol group, it can react with an electrophilic group present on the binding polymer (e.g., an epoxy, anhydride, activated ester group) to produce a covalent bond.

In a further aspect, the blocking agent comprises an alkyl amine, an alkylhydroxy amine, or an alkoxyalkyl amine. The term "alkyl" as used herein is a branched or unbranched saturated hydrocarbon group of 1 to 25 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. Examples of longer chain alkyl groups include, but are not limited to, an oleate group or a palmitate group. A "lower alkyl" group is an alkyl group containing from one to six carbon atoms. The term "alkylhydroxy" as used herein is an alkyl group as defined above where at least one of the hydrogen atoms is substituted with a hydroxyl group. The term "alkylalkoxy" as used herein is an alkyl group as defined above where at least one of the hydrogen atoms is substituted with an alkoxy group —OR, where R is an alkyl group as defined above.

In a further aspect, the blocking agent comprises ammonia, 2-(2-aminoethoxy)ethanol, N,N-dimethyl ethylenediamine, ethanolamine, ethylenediamine, hydroxyl amine, methoxyethyl amine, ethyl amine, isopropyl amine, butyl amine, propyl amine, hexyl amine, 2-amino-2-methyl-1-propanol, 2-(2-aminoethyl amino) ethanol, 2-(2-aminoethoxy)ethanol, dimethylethanolamine, dibutyl ethanolamine, 1-amino-2-propanol, polyethylene glycol, polypropylene glycol, 4,7,10-trioxa-1,13-tridecanediamine, polyethylene glycol or an amine-terminated-polyethylene glycol, Trizma hydrochloride, or any combination thereof. In another aspect, the blocking agent comprises water, $H_2S$, an alcohol (ROH), or alkyl thiol (RSH), where R is an alkyl group as defined above.

The supports described herein with the ratio of reactive groups to ionizable groups present on the binding polymer possess numerous advantages over prior art sensors. The ratio of reactive groups to ionizable groups permits increased loading or attachment (directly or indirectly with the use of a tie layer) of the binding polymer to the substrate. As will be discussed below, the attachment of the binding polymer to the substrate involves mild conditions and does not require pre-activation with, for example, EDC/NHS. This ultimately saves time and costs with respect to manufacturing the supports. It is also possible to control the ratio of reactive groups/ionizable groups with other properties of the binding polymer such as hydrophobicity/hydrophilicity, which can ultimately increase the efficiency of the support.

Another feature associated with the supports described herein is the higher binding capacity between the support and the biomolecule. It is believed that if more binding polymer can be loaded on the substrate then more biomolecule can be attached to the binding polymer. Once again, if more biomolecules can be attached to the substrate, the performance of the support is also enhanced. In certain aspects, once the biomolecule is attached to the binding polymer, the immobilized biomolecule is more available for binding. For example, immobilized proteins are less sterically hindered relative to when they are immobilized on supports of the present invention when compared to supports that do not possess the ratio of reactive groups to ionizable groups as recited herein. Additionally, the binding polymers described herein have greater flexibility, which also permit greater binding between the binding polymer and the biomolecule. Ultimately, the binding polymers used herein provide increased binding assay sensitivity/signal-to-noise ratios, which is a very desirable feature when conducting assays of biomolecules.

d. Preparation of Supports

The amount of binding polymer attached to the substrate can vary depending upon among other things the selection of the binding polymer, the biomolecule, and the analyte to be detected. In one aspect, the binding polymer comprises at least one monolayer. In a further aspect, the binding polymer has a thickness of about 100 Å to about 2,000 Å. In another aspect, the thickness of the binding polymer has a lower endpoint of 10 Å, 20 Å 40 Å, 60 Å, 80 Å, 100 Å, 150 Å, 200 Å, 300 Å, 400 Å, or 500 Å and an upper endpoint of 750 Å, 1,000 Å, 1,250 Å, 1,500 Å, 1,750 Å, or 2,000 Å, where any lower endpoint can be combined with any upper endpoint to form the thickness range.

The binding polymer can be attached to the substrate using techniques known in the art. For example, the substrate can be dipped in a solution of the binding polymer. In another aspect, the binding polymer can be sprayed, vapor deposited, screen printed, or robotically pin printed or stamped on the substrate. This could be done either on a fully assembled substrate or on a bottom insert (e.g., prior to attachment of the bottom insert to a holy plate to form a microplate).

In a further aspect, the support can be made by attaching a binding polymer directly or indirectly to the substrate, wherein the binding polymer has a plurality of reactive groups capable of attaching to a biomolecule. When the binding polymer is directly or indirectly attached to the substrate, the binding polymer can be attached either covalently or non-covalently (e.g., electrostatic). FIG. 1 depicts one aspect of the attachment of the binding polymer to the substrate, where the nucleophilic group Z (e.g., an amino group, hydroxyl group, or thiol group) reacts with an anhydride group of the binding polymer to produce a new covalent bond.

In another aspect, when the binding polymer is indirectly attached to the substrate, a tie layer can be used. The tie layer can be covalently or electrostatically attached to the outer surface of the substrate. The term "outer surface" with respect to the substrate is the region of the substrate that is exposed and can be subjected to manipulation. For example, any surface on the substrate that can come into contact with a solvent or reagent upon contact is considered the outer surface of the substrate. Thus, the tie layer can be attached to the substrate and the binding polymer.

In various aspects, the substrates described herein have a tie layer covalently bonded to the substrate; however, it is also contemplated that a different tie layer can be attached to the substrate by other means in combination with a tie layer that is covalently bonded to the substrate. For example, one tie layer can be covalently bonded to the substrate and a second tie layer can be electrostatically bonded to the substrate. In a further aspect, when the tie layer is electrostatically bonded to the substrate, the compound used to make the tie layer is positively charged and the outer surface of the substrate is treated such that a net negative charge exists so that tie layer compound and the outer surface of the substrate form an electrostatic bond.

In a further aspect, the outer surface of the substrate can be derivatized so that there are groups capable of forming a covalent bond with the tie layer. The tie layer can be directly or indirectly covalently bonded to the substrate. In the case when the tie layer is indirectly bonded to the substrate, a linker possessing groups that can covalently attach to both the substrate and the tie layer can be used. Examples of linkers include, but are not limited to, an ether group, a polyether group, a polyamine, or a polythioether. If a linker is not used, and the tie layer is covalently bonded to the substrate, this is referred to as direct covalent attachment.

In a further aspect, the tie layer is derived from a compound comprising one or more reactive functional groups that can react with the binding polymer. The phrase "derived from" with respect to the tie layer is defined herein as the resulting residue or fragment of the tie layer compound when it is attached to the substrate. The functional groups permit the attachment of the binding polymer to the tie layer. In a further aspect, the functional groups of the tie layer compound comprises an amino group, a thiol group, a hydroxyl group, a carboxyl group, an acrylic acid, an organic and inorganic acid, an activated ester, an anhydride, an aldehyde, an epoxide, an isocyanate, an isothiocyanate, their derivatives or salts thereof, or a combination thereof.

In one aspect, the substrate is amine-modified with, for example, a polymer comprising at least one amino group. Examples of such polymers include, but are not limited to, poly-lysine, polyethylenenimine, poly(allyl)amine, or silylated polyethylenenimine. In another aspect, the substrate is modified with an aminosilane. In a further aspect, the tie layer is derived from a straight or branched-chain aminosilane, aminoalkoxysilane, aminioalkylsilane, aminoarylsilane, aminoaryloxysilane, or a derivative or salt thereof. In a further aspect, the tie layer is derived from 3-aminopropyl trimethoxysilane, N-(beta-aminoethyl)-3-aminopropyl trimethoxysilane, N-(beta-aminoethyl)-3-aminopropyl triethoxysilane, N'-(beta-aminoethyl)-3-aminopropyl methoxysilane, or aminopropylsilsesquixoxane.

In another aspect, when the substrate is composed of gold, the binding polymer is attached to the substrate by an aminothiol such as, for example, 11-amino-1-undecanethiol hydrochloride.

The tie layer can be attached to any of the substrates described herein using techniques known in the art. For example, the substrate can be dipped in a solution of the tie layer compound. In a further aspect, the tie layer compound can be sprayed, vapor deposited, screen printed, or robotically pin printed or stamped on the substrate. This could be done either on a fully assembled substrate or on a bottom insert (e.g., prior to attachment of the bottom insert to a holy plate to form a microplate).

In one aspect, the substrate comprises a gold chip, the binding polymer comprises poly(ethylene-alt-maleic anhydride) indirectly attached to the substrate by an aminothiol, and the ratio of reactive groups to ionizable groups in the binding polymer is from 0.67 to 3.0. In another aspect, the substrate comprises a glass substrate with a layer comprising $Ta_2O_5$, $Nb_2O_5$, $TiO_2$, $Al_2O_3$, silicon nitride, $SiO_2$ or a mixture thereof the binding polymer comprises poly(ethylene-alt-maleic anhydride) indirectly attached to the substrate by a tie layer, wherein the tie layer is derived from aminopropylsilane (e.g., gamma-aminopropylsilane), and the ratio of reactive groups to ionizable groups in the binding polymer is from 0.67 to 3.0. In the aspects above, the poly(ethylene-alt-maleic anhydride) is preblocked with methoxyethyl amine prior to attaching the polymer to the substrate.

II. Methods of Use

Described herein are methods for assaying an analyte. In one aspect, the method comprises:

a. contacting the sample comprising the analyte with a support comprising a substrate and a binding polymer directly or indirectly attached to the substrate, wherein the binding polymer has a plurality of reactive groups capable of attaching to a biomolecule and a plurality of ionizable groups, wherein the ratio of reactive groups to ionizable groups is from 0.5 to 10, and b. detecting the bound analyte.

It is contemplated that one or more different biomolecules can be attached to the substrate to produce a variety of biological sensors. In a further aspect, the biomolecule can be attached covalently or electrostatically to the binding polymer. The biomolecules may exhibit specific affinity for another molecule through covalent or non-covalent bonding. Examples of biomolecules useful herein include, but are not limited to, a nucleic acid molecule, an antibody, a peptide, a small molecule, a lectin, a modified polysaccharide, a synthetic composite macromolecule, a functionalized nanostructure, a synthetic polymer, a modified/blocked nucleotides/nucleoside, a modified/blocked amino acid, a fluorophore, a chromophore, a ligand, a chelate, an aptamer, a drug (e.g., a small molecule), or a hapten.

In a further aspect, the biomolecule can be a protein. For example, the protein can include peptides, fragments of proteins or peptides, membrane-bound proteins, or nuclear proteins. The protein can be of any length, and can include one or more amino acids or variants thereof. The protein(s) can be fragmented, such as by protease digestion, prior to analysis. A protein sample to be analyzed can also be subjected to fractionation or separation to reduce the complexity of the samples. Fragmentation and fractionation can also be used together in the same assay. Such fragmentation and fractionation can simplify and extend the analysis of the proteins.

In a further aspect, the biomolecule is a virus. Examples of viruses include, but are not limited to, Herpes simplex virus type-1, Herpes simplex virus type-2, Cytomegalovirus, Epstein-Barr virus, Varicella-zoster virus, Human herpesvirus 6, Human herpesvirus 7, Human herpesvirus 8, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency cirus, Human T-cell Leukemia virus type-1, Hantavirus, Rubella virus, Simian Immunodeficiency virus, Human Immunodeficiency virus type-1, Vaccinia virus, SARS virus, Human Immunodeficiency virus type-2, lentivirus, baculovirus, adeno-associated virus, or any strain or variant thereof.

In a further aspect, the biomolecule comprises a nucleic acid. The nucleic acid can be an oligonucleotide, deoxyribonucleic acid (DNA) or a fragment thereof, ribonucleic acid (RNA) or a fragment thereof, or peptide nucleic acid (PNA) or a fragment thereof. The nucleic acid can be a nucleic acid from any source, such as a nucleic acid obtained from cells in which it occurs in nature, recombinantly produced nucleic acid, or chemically synthesized nucleic acid. For example, the nucleic acid can be cDNA or genomic DNA or DNA synthesized to have the nucleotide sequence corresponding to that of naturally-occurring DNA. The nucleic acid can also be a mutated or altered form of nucleic acid (e.g., DNA that differs from a naturally occurring DNA by an alteration, deletion, substitution or addition of at least one nucleic acid residue) or nucleic acid that does not occur in nature.

In a further aspect, the nucleic acid can be present in a vector such as an expression vector (e.g., a plasmid or viral-based vector). In a further aspect, the vector is a chromosomally integrated vector. The nucleic acids useful herein can be linear or circular and can be of any size. In a further aspect, the nucleic acid can be single or double stranded DNA or RNA.

In a further aspect, the nucleic acid can be a functional nucleic acid. Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, RNAi, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Once the binding polymer has been attached to the substrate, one or more biomolecules can be attached to the binding polymer using the techniques presented above. In a further aspect, when the biomolecule is a nucleic acid or protein, the nucleic acid or protein can be printed on the binding polymer using techniques known in the art. The amount of biomolecule that can be attached to the polymer layer can vary depending upon among other things, for example, the biomolecule and binding polymer selected and the analyte to be detected. In a further aspect, one or more different biomolecules can be placed at different locations on the support. In the case when different biomolecules are used, the biomolecules can be printed at the same time or different time.

In a further aspect, the biomolecule can be deposited on (i.e., attached to) the support by immersing the tip of a pin into the composition comprising the biomolecule; removing the tip from the composition, wherein the tip comprises the composition; and transferring the composition to the support. This aspect can be accomplished, for example, by using a typographic pin array. The depositing step can be carried out using an automated, robotic printer. Such robotic systems are available commercially from, for example, Intelligent Automation Systems (IAS), Cambridge, Mass.

The pin can be solid or hollow. The tips of solid pins are generally flat, and the diameter of the pins determines the volume of fluid that is transferred to the substrate. Solid pins having concave bottoms can also be used. In one aspect, to permit the printing of multiple arrays with a single sample loading, hollow pins that hold larger sample volumes than solid pins and therefore allow more than one array to be printed from a single loading can be used. Hollow pins include printing capillaries, tweezers and split pins. An example of a preferred split pen is a micro-spotting pin that TeleChem International (Sunnyvale, Calif.) has developed. In one aspect, pins made by Point Tech can be used herein. The spotting solutions described herein can be used in a number of commercial spotters including, but not limited to, Genetix and Biorobotics spotters.

Any of the supports described herein with one or more biomolecules attached thereto can be used to assay an analyte upon contact of the analyte with the support. Upon contact of the analyte with the support, a chemical interaction between the biomolecule and the analyte occurs to produce a bound analyte; however, it is possible that an interaction may occur to some extent between the binding polymer and the analyte. The nature of the interaction between the biomolecule and the analyte will vary depending upon the biomolecule and the analyte selected. In one aspect, the interaction between the biomolecule and the analyte can result in the formation of an electrostatic bond, a hydrogen bond, a hydrophobic bond, or a covalent bond. In another aspect, an electrostatic interaction can occur between the biomolecule and the analyte.

The analyte can be any naturally-occurring or synthetic compound. Examples of analytes that can be bound to the biomolecules on the substrate include, but are not limited to, a drug, an oligonucleotide, a nucleic acid, a protein, a peptide, an antibody, an antigen, a hapten, or a small molecule (e.g., a pharmaceutical drug). Any of the biomolecules described above can be an analyte for the methods described herein. In one aspect, a solution of one or more analytes is prepared and added to one or more wells that have a biomolecule attached to the outer surface of the microplate. In this aspect, it is contemplated that different biomolecules can be attached to different wells of the microplate; thus, it is possible to detect a number of different interactions between the different biomolecules and the analyte. In one aspect, a protein can be immobilized on the microplate to investigate the interaction between the protein and a second protein or small molecule. Alternatively, a small molecule can be immobilized on the microplate using the techniques described herein to investigate the interaction between the small molecule and a second small molecule or protein. In a further aspect, the biomolecule can be an oligonucleotide that can hybridize a second oligonucleotide (i.e., analyte). In a further aspect, when the substrate is a microplate, the assay can be a high-throughput assay.

In a further aspect, an array can be used in any of the methods described herein. In one aspect, the array comprises a plurality of biomolecules on the substrate, wherein the biomolecules are on discrete and defined locations on the support. Arrays have been used for a wide range of applications such as gene discovery, disease diagnosis, drug discovery pharmacogenomics) and toxicological research (toxicogenomics). An array is an orderly arrangement of biomolecules. The typical method involves contacting an array of biomolecules with a target of interest to identify those compounds in the array that bind to the target. Arrays are generally described as macro-arrays or micro-arrays, the difference being the size of the sample spots. In one aspect, the array comprises at least 96 or 384 distinct and defined locations.

Methods for producing arrays are known in the art. For example, Fodor et al., 1991, Science 251:767-773 describe an in situ method that utilizes photo-protected amino acids and photo lithographic masking strategies to synthesize miniaturized, spatially-addressable arrays of peptides. This in situ method has recently been expanded to the synthesis of miniaturized arrays of oligonucleotides (U.S. Pat. No. 5,744, 305). Another in situ synthesis method for making spatially-addressable arrays of immobilized oligonucleotides is described by Southern, 1992, Genomics 13:1008-1017; see also Southern & Maskos, 1993, Nucl. Acids Res. 21:4663-4669; Southern & Maskos, 1992, Nucl. Acids Res. 20:1679-1684; Southern & Maskos, 1992, Nucl. Acids Res. 20:1675-1678. In this method, conventional oligonucleotide synthesis reagents are dispensed onto physically masked glass slides to create the array of immobilized oligonucleotides. U.S. Pat. No. 5,807,522 describes a deposition method for making micro arrays of biological samples that involves dispensing a known volume of reagent at each address of the array by tapping a capillary dispenser on the substrate under conditions effective to draw a defined volume of liquid onto the substrate.

In one aspect, an array of nucleic acid(s) or protein(s) can be printed on any of the substrates described herein. The techniques disclosed in U.S. Published Application No. 2003/0228601 to Sabatini can be used herein, which is incorporated by reference with respect to the different arrays and nucleic acid libraries that can be used in the methods described herein.

In another aspect, the supports described herein have a surface with both a reference region and a sample region. Several different deposition techniques (e.g. contact pin printing, non-contact printing, microcontact printing, screen printing, spray printing, stamping, spraying,) can be used to create a reference region and a sample region on a single support. The sample region permits the detection of an interaction between an analyte and the immobilized biomolecule, while the reference region permits the cancellation of spurious changes that can adversely affect the detection of the interaction between the analyte and immobilized biomolecule. In one embodiment, the sample and reference regions are incorporated within a well of a microplate.

In one aspect, a predefined area of the support with the binding polymer is specifically deactivated by depositing a blocking/deactivating agent. For example, when the binding polymer is an amine reactive coating such as EMA, any of the blocking agents described above can be used as the deactivating agent. Alternatively, non-amine containing reagents could be used to hydrolyze the reactive group present on the binding polymer to render it inactive. Thus, the biomolecule only binds to the sensor in the area that was not treated with the deactivating agent.

In another aspect, the biomolecule is attached to the binding polymer, and the support is exposed to a deactivating agent to inactivate/block the unprinted regions of the support, which can be used as reference regions.

Once the support with the attached biomolecules(s) has been contacted with the analyte, the bound analyte is detected. As described above, one of the advantages of the substrates described herein is that non-specific binding of the analyte is reduced.

In a further aspect, the bound analyte can be labeled for detection purposes. Depending upon the detection technique used, in one aspect, the analyte can be labeled with a detectable tracer prior to detection. The interaction between the analyte and the detectable tracer can include any chemical or physical interaction including, but not limited to, a covalent bond, an ionic interaction, or a Lewis acid-Lewis base interaction. A "detectable tracer" as referred to herein is defined as any compound that (1) has at least one group that can interact with the analyte as described above and (2) has at least one group that is capable of detection using techniques known in the art. In a further aspect, the analyte can be labeled prior to contacting the support. In another aspect, the analyte can be labeled after it has been contacted with the support. Examples of detectable tracers include, but are not limited to, fluorescent and enzymatic tracers.

In another aspect, detection of the bound analyte can be accomplished with other techniques including, but not limited to, fluorescence, phosphorescence, chemilumenescence, bioluminescence, Raman spectroscopy, optical scatter analysis, mass spectrometry, etc. and other techniques generally known to those skilled in the art. In a further aspect, the bound analyte is detected by label-independent detection or LID. Examples of LID include, but are not limited to, a refractive index sensor (e.g., surface plasmon resonance, a resonant waveguide grating system, or ellipsometry), an acoustic wave sensor, or a mass sensor such as mass spectrometry or a quartz crystal microbalance.

In summary, the supports and methods described herein permit the loading of high amounts of biomolecules, which leads to better sensitivity with respect to detecting an analyte. The supports and methods described herein are also compatible with a number of different substrates, which has a broad range of applications. The preparation of the supports require mild conditions, and the resultant supports exhibit good storage stability coupled with consistent, reproducible attachment of biomolecules to the substrate. Finally, the supports and methods also increase array signal intensity, sensitivity and assay quality in a timely and economical manner and further improve the assay specificity.

EXAMPLES

The following examples are put forth so as to provide those of ordinary skill in the art with a complete disclosure and description of how the materials, articles, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Figure 13:
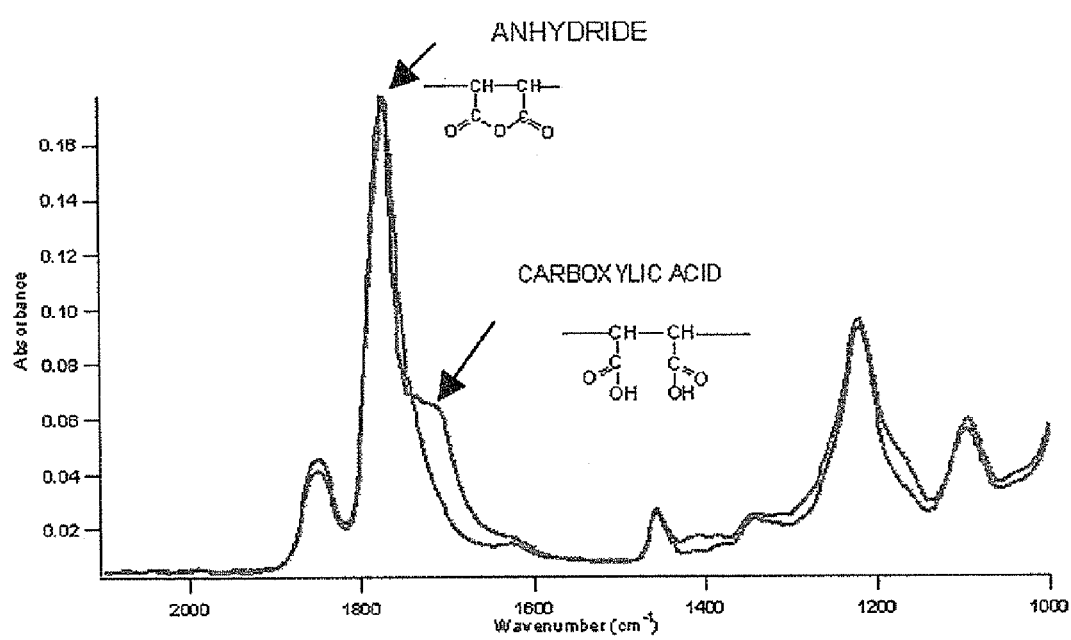
FIG. 13 shows FTIR spectra of partially hydrolyzed EMA and EMA vacuum dried at 140° C. for 1 hour.

Preparation of Pre-Blocked Ethylene Maleic Anhydride Copolymers with Ethanolamine FIG. 13 shows the FTIR spectra of poly(ethylene-alt-maleic anhydride) (EMA) partially hydrolyzed and vacuum-dried at 140° C. for one hour. The spectrum of the partially hydrolyzed EMA shows clearly the presence of carboxylic acid groups (shoulder at 1790 cm$^{-1}$) due to hydrolysis occurring upon storage. The spectrum after vacuum-dried EMA shows that all the carboxylic groups were converted to the anhydride (no shoulder visible). This carboxylic acid free EMA is particularly suitable as raw material to ensure a well-controlled pre-blocking reaction.

Dry EMA purchased from Sigma Aldrich (ref 18, 805-0) (0.2 g) was dissolved in 14.80 g anhydrous 1-methyl-2-pyrrolidinone (NMP) under stirring for about 1 hour. In parallel, a solution of ethanolamine was prepared by adding 239 µl of pure ethanolamine in 50 g of anhydrous NMP. Then, 5 g of the ethanolamine/NMP solution, which corresponds to the amount required to pre-block about 25 mol % of the anhydride groups based on the feed composition, was added as quickly as possible to the solution of EMA. After gentle stirring for 3 hours at room temperature, 2 g of this solution was added to 18 g of anhydrous isopropyl alcohol (IPA) and stirred.

The same procedure was repeated except that the appropriate amount of ethanolamine/NMP solution was added in order to pre-block at 15, 20 and 30 mole % of maleic anhydride groups, keeping constant the solid content of the solutions. 0% preblocking was made using the same procedure but adding no ethanolamine.

Example 2

Preparation of Gold Sensor Chip for SPR Detection

Biacore gold sensor chips were cleaned by rinsing with ethanol and water and then dried under a gentle stream of nitrogen. The chips were soaked for one hour in a 1 mM ethanolic solution of 1-mercaptoundecylamine, rinsed with ethanol, then with water, and finally dried under a stream of nitrogen.

Silicone gasket (Flexiperm) was applied onto each gold chip and 100 µl of the pre-blocked EMA solutions from Example 1 were added per well. After 10 min of coupling, the chips were rinsed with ethanol and dried with a stream of nitrogen. After drying the silicone gasket was removed. At this point the coated gold chips are ready for immobilization of the biomolecules without the need of any activation step.

Example 3

Preparation of LID Coated Plate

A 5 wt % solution of aminopropylsilsesquioxane (APS) in deionized water was prepared from the 20 wt % commercially available solution. 100 µl of this diluted solution was added in each well and then incubated for 10 minutes. After incubation, the APS solution was removed, the plate was rinsed three times with water and three times with ethanol then dried with a gentle stream of nitrogen.

After drying, 100 µl of the pre-blocked ethylene-alt-maleic anhydride copolymer solution from Example 1 was added to the wells and incubated for 10 minutes at room temperature. The excess solution was removed, and the plate was rinsed three times with ethanol. After rinsing, the plate was dried by a gentle nitrogen stream. At this point the plate is ready for use without any further activation.

Example 4

Protein (Strepatavidin) Immobilization on a Gold Sensor Chip

The coated gold sensor from Example 2 was introduced in a Biacore SPR device. The two flow cells were flushed with 5 mM sodium acetate at pH 5.5 for a few minutes at 5 µl/min and then 35 µl of 250 µg/ml solution of streptavidin (SA) in 5 mM sodium acetate was injected at 5 µl/min for 7 min in one flow cell. The two flow cells were blocked with 200 mM ethanolamine in 50 mM borate buffer (pH 9) and rinsed with 0.05% Tween 20 in PBS.

Figure 2:
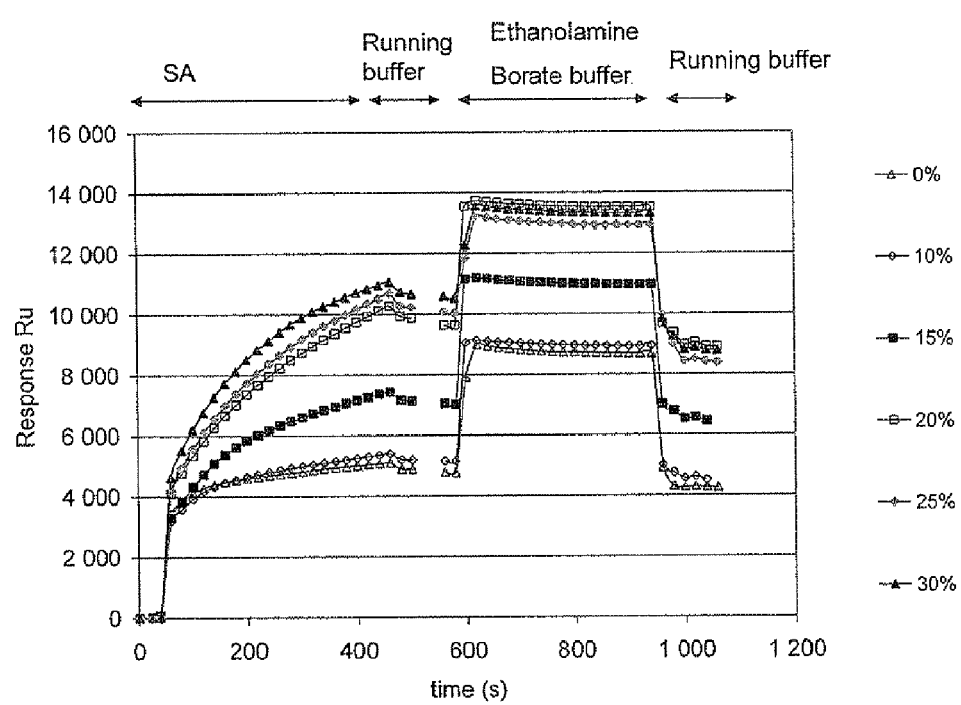
FIG. 2 shows SA immobilized SPR response curves on gold chips coated with EMA pre-blocking with ethanolamine at 0, 10, 15, 20, 25, and 30 mole %.

FIG. 2 shows the SA immobilization curve on gold chips coated with EMA pre-blocked at 0, 10, 15, 20, 25, 30 mole % respectively. The strong effect of the pre-blocking is clearly visible. The sensor surface coated with pre-blocked EMA at 20, 25, and 30% exhibit two times higher streptavidin immobilization than with unblocked EMA.

Example 5

SPR Evaluation of Small Molecule Binding to the Immobilized Protein

Figure 3:
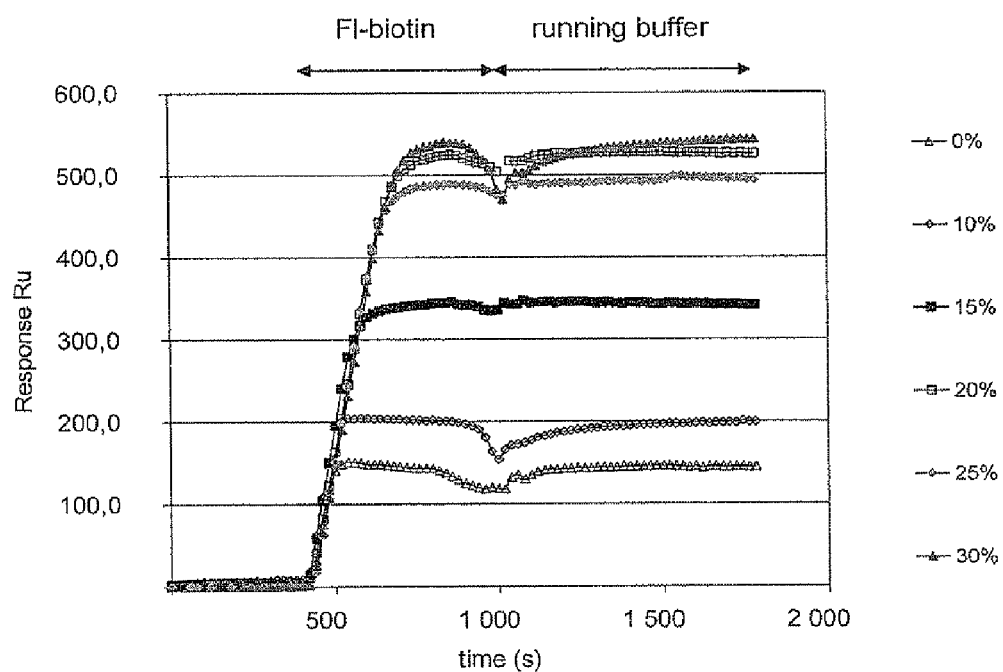
FIG. 3 shows the binding curve for 4-fl Biotin binding to immobilized SA for supports made of EMA with different degree of pre-blocking with ethanolamine compared to EMA without pre-blocking.
Figure 11:
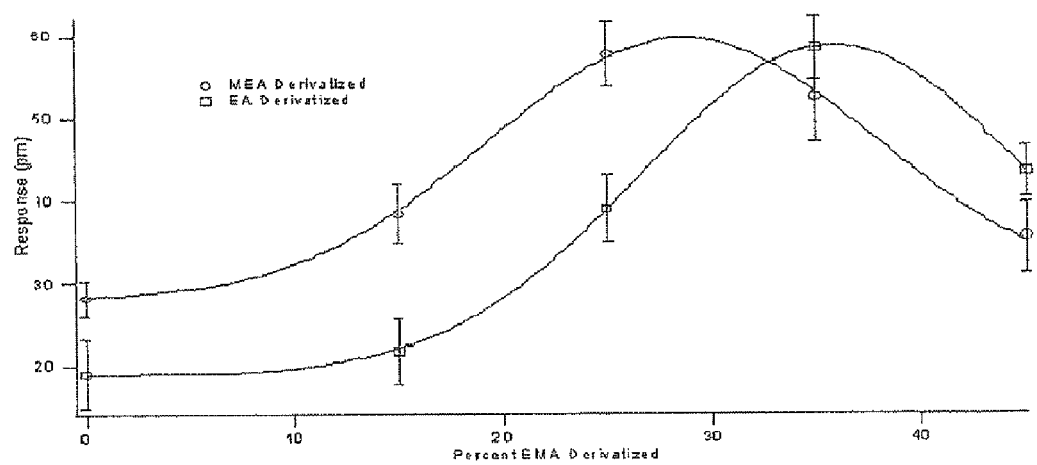
FIG. 11 shows the optimum value of pre-blocking with ethanolamine and methoxyethylamine for the fl-biotin binding assay using the Corning Epic™ System.
Figure 12:
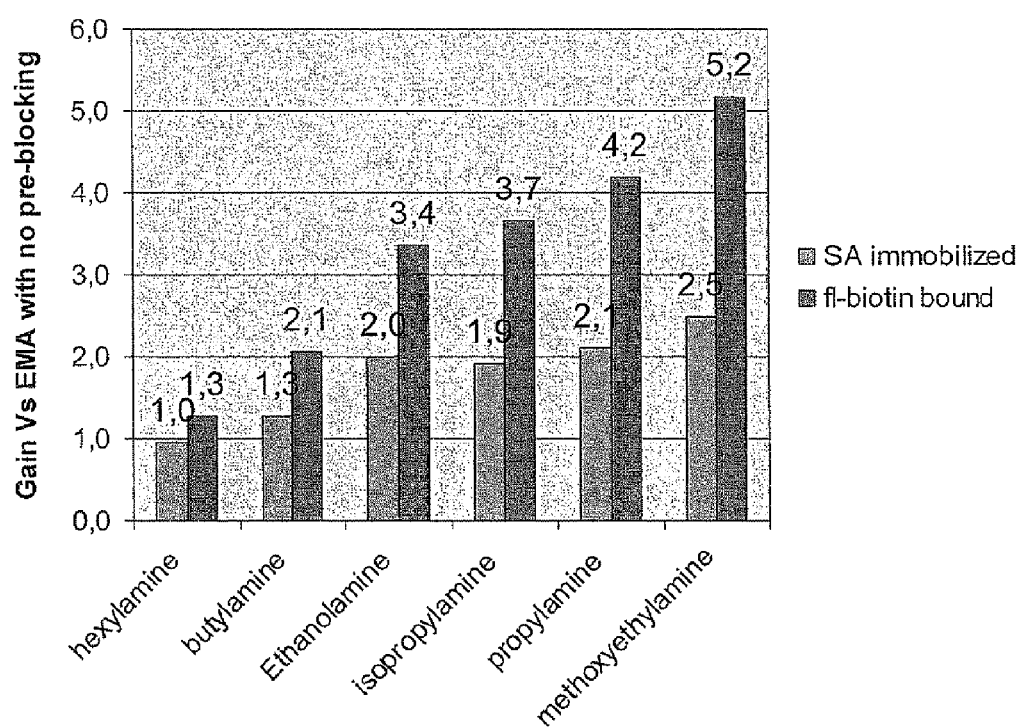
FIG. 12 shows the impact of the pre-blocking agent on both Streptavidin immobilization and fl-biotin binding.

In order to evaluate the biotin binding capacity, each chip on which SA was immobilized in Example 4 was used to perform the binding assay. Biotin binding was monitored using 100 µl of a 100 nM solution of 4-Fluorescein-Biotin in acetate buffer at 10 µl/min for 10 min. A flow cell free of Streptavidin and blocked with ethanolamine was used as a reference. FIG. 3 shows the binding curves obtained for 4-fl Biotin binding to immobilized SA on sensors surfaces made of EMA with different degrees of pre-blocking compared to EMA without pre-blocking after the reference had been subtracted out. FIG. 11 shows the optimum value of pre-blocking with ethanolamine for the fl-biotin binding assay using Corning's Epic™ System for detection. FIG. 12 shows the impact of ethanolamine as the pre-blocking agent on both Streptavidin immobilization and fl-biotin binding vs. EMA with no pre-blocking.

Results obtained from Examples 4 and 5 prove the better "accessibility for small molecule binding" of the protein immobilized with the support of the invention. Data are summarized in the table given below. The data demonstrate that the ratio of small molecule bound per protein immobilized increases when the pre-blocking increases.

| % blocking | Reactive/ ionizable | Immobilized protein (Ex. 4) | Small molecule binding (Ex. 5) | Small molecule/ protein |
|---|---|---|---|---|
| 0 | — | 4,000 | 140 | 0.035 |
| 15 | 5.66 | 6,500 | 340 | 0.052 |
| 20 | 4.00 | 9,000 | 525 | 0.058 |

Example 6

Figure 4:
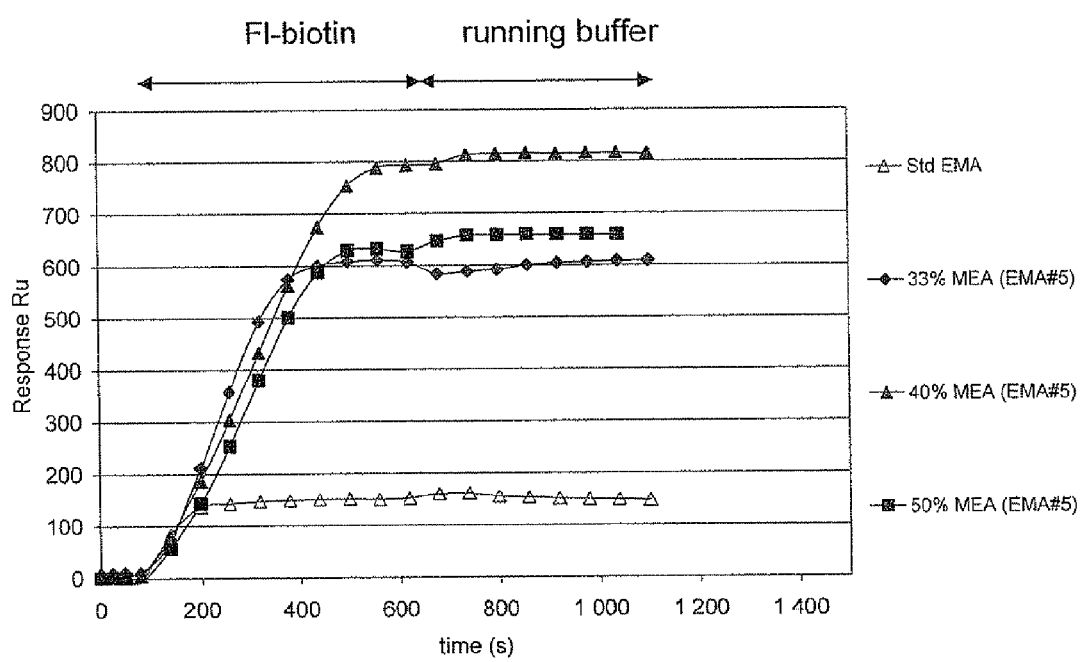
FIG. 4 shows the effect of pre-blocking with methoxyethylamine on 4-fl biotin binding.

Preparation of Pre-Blocked Ethylene-Alt-Maleic Anhydride Copolymers with Methoxyethyl Amine, Immobilization of SA and Small Molecule Binding Assay The same procedure as described in Example 2 was reproduced but ethanolamine was replaced by methoxyethylamine and the degree of pre-blocking of the maleic anhydride copolymer was 33, 40, and 55 mole % based on the feed composition. Immobilization of SA was conducted as described in Example 4. Evaluation of small molecule binding on immobilized protein was performed according to Example 5. FIG. 4 shows the effect of pre-blocking with methoxyethylamine on 4-fl biotin binding. FIG. 13 shows the optimum value of pre-blocking with methoxyethylamine for the fl-biotin binding assay using LID detection. FIG. 12 shows the impact of methoxyethylamine as the pre-blocking agent on both Streptavidin immobilization and fl-biotin binding vs. EMA with no pre-blocking.

Example 7

Figure 5:
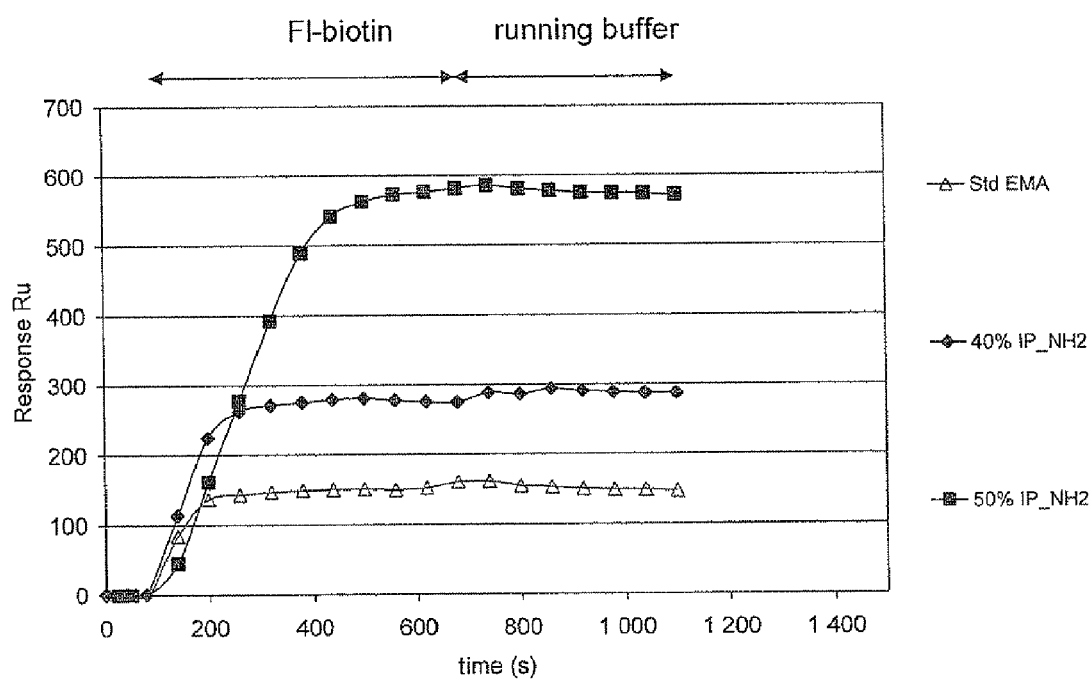
FIG. 5 show the effect of pre-blocking with isopropylamine on 4-fl biotin binding.

Preparation of Pre-Blocked Ethylene-Alt-Maleic Anhydride Copolymers with Isopropyl Amine, Immobilization of SA and Small Molecule Binding Assay The same procedure as described in Example 1 was used but ethanolamine was replaced by isopropylamine and the degree of pre-blocking of the ethylene-alt-maleic anhydride copolymer was 40 and 50 mole % based on the feed composition. Immobilization of SA was performed as described in Example 4. Evaluation of small molecule binding on immobilized protein SA was performed according to Example 5. FIG. 5 shows the effect of pre-blocking with isopropylamine on 4-fl biotin binding. FIG. 12 shows the impact of isopropyl amine as the pre-blocking agent on both Streptavidin immobilization and fl-biotin binding vs. EMA with no pre-blocking.

Example 8

Preparation of Pre-Blocked Ethylene-Alt-Maleic Anhydride Copolymers with Butylamine, Immobilization of SA and Small Molecule Binding Assay

Figure 6:
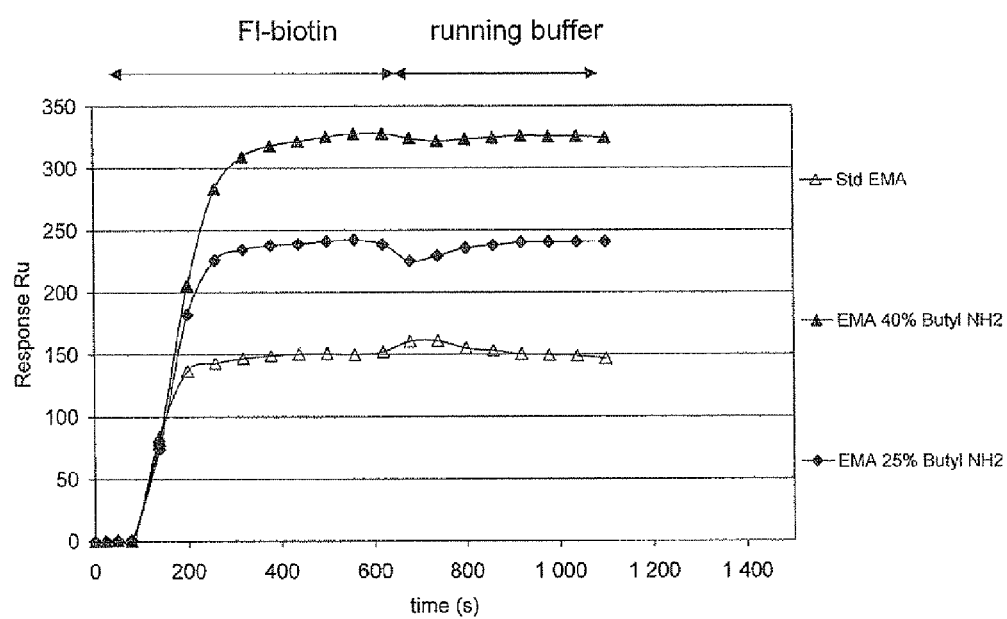
FIG. 6 shows the effect of pre-blocking with butylamine on 4-fl biotin binding.

The same procedure as described in Example 1 was used but ethanolamine was replaced with butylamine and the degree of pre-blocking of the ethylene-alt-maleic anhydride copolymer was 25 and 40 mole % based on the feed composition. Immobilization of SA was performed as described in Example 4. Evaluation of small molecule binding on immobilized protein was performed according to Example 5. FIG. 6 shows the effect of pre-blocking with butylamine on 4-fl biotin binding. FIG. 12 shows the impact of butyl amine as the pre-blocking agent on both Streptavidin immobilization and fl-biotin binding vs. EMA with no pre-blocking.

Example 9

Preparation of Pre-Blocked Ethylene-Alt-Maleic Anhydride Copolymers with Propyl Amine, Immobilization of SA and Small Molecule Binding Assay

Figure 7:
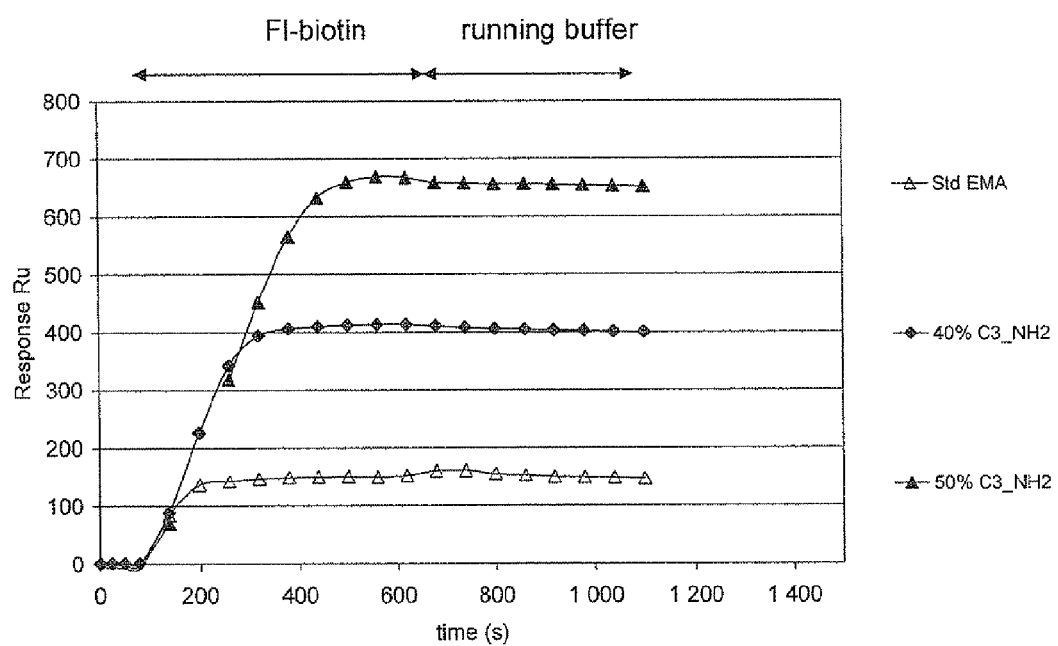
FIG. 7 shows the effect of pre-blocking with propylamine on 4-fl biotin binding.

The same procedure as described in Example 1 was used but ethanolamine was replaced with propyl amine and the degree of pre-blocking of the ethylene-alt-maleic anhydride copolymer was 40 and 50 mole % based on the feed composition. Immobilization of SA was performed as described in Example 4. Evaluation of small molecule binding on immobilized protein was performed according to Example 5. FIG. 7 shows the effect of pre-blocking with propyl amine on 4-fl biotin binding. FIG. 12 shows the impact of propyl amine as the pre-blocking agent on both Streptavidin immobilization and fl-biotin binding vs. EMA with no pre-blocking.

Example 10

Preparation of Pre-Blocked Ethylene-Alt-Maleic Anhydride Copolymers with Hexyl Amine

Figure 8:
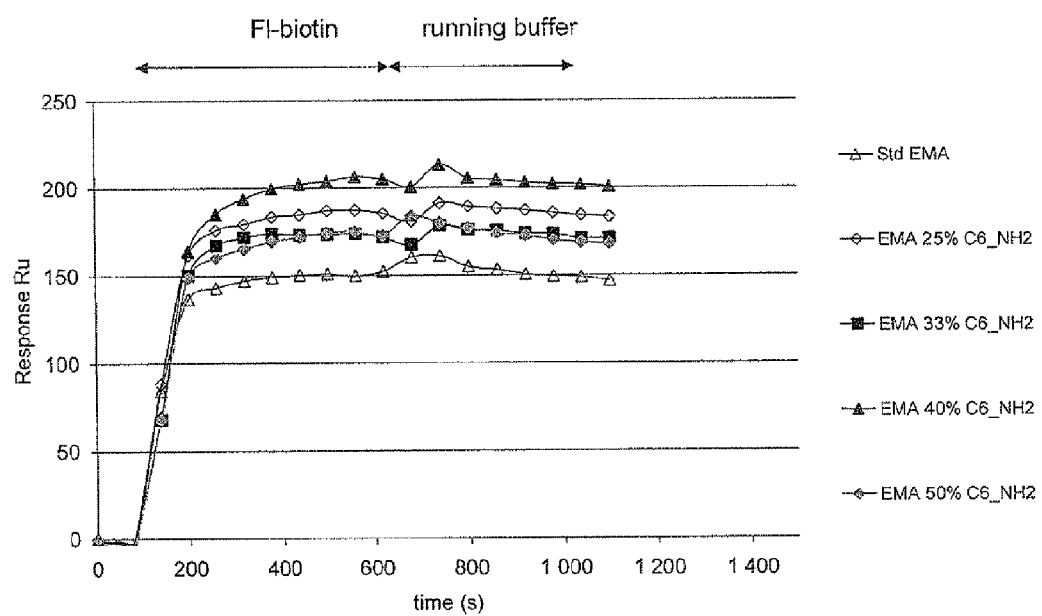
FIG. 8 shows the effect of pre-blocking with hexylamine on 4-fl biotin binding.

The same procedure as described in Example 1 was used but ethanolamine was replaced by hexylamine and the degree of pre-blocking of the ethylene-alt-maleic anhydride copolymer was 0, 25, 33, 40 and 50 mole % based on the feed composition. Immobilization of SA was performed as described in Example 4. Evaluation of small molecule binding on immobilized protein was performed according to Example 5. FIG. 8 shows the effect of pre-blocking with hexyl amine on 4-fl biotin binding. FIG. 12 shows the impact of hexyl amine as the pre-blocking agent on both Streptavidin immobilization and fl-biotin binding vs. EMA with no pre-blocking.

Example 11

Preparation of Pre-Blocked Ethylene-Alt-Maleic Anhydride Copolymers with Ethanolamine and Corning Epic™ System (Binding of fl-Biotin to Immobilized Streptavidin) Assay Performed on Corning Epic™ Microplate

Figure 9:
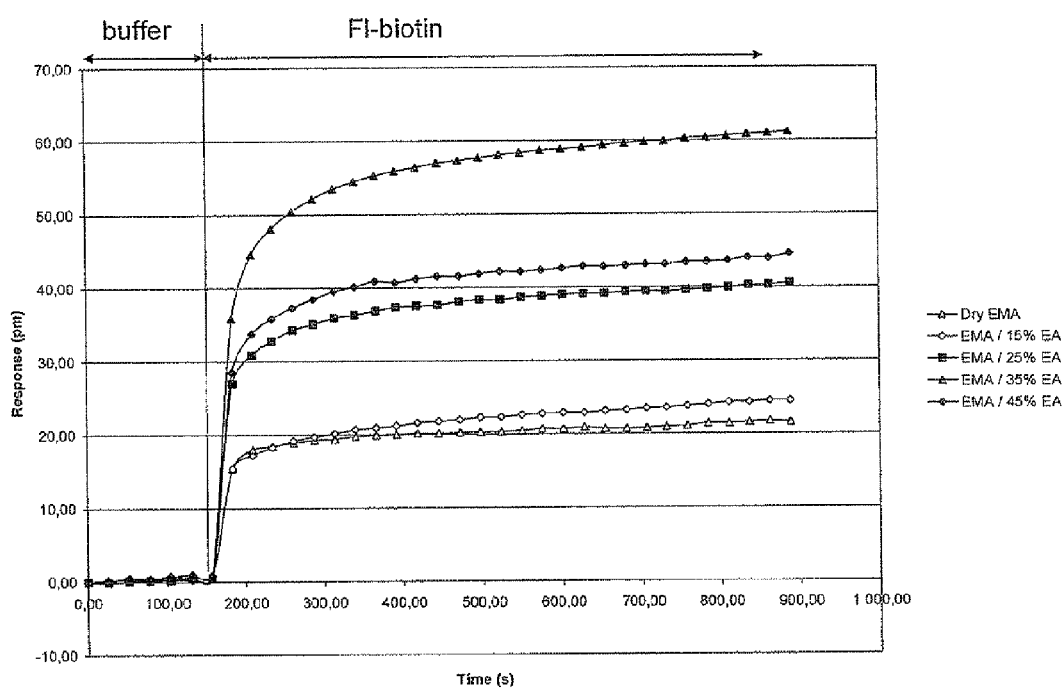
FIG. 9 shows binding curves from the Corning Epic™ System for the fl-biotin assay with plates coated with maleic anhydride copolymers pre-blocked with ethanolamine at different pre-blocking degrees.

Pre-blocked EMA with ethanolamine having pre-blocking degrees of 15, 25, 35, 45 mole % were prepared according to the procedure described in Example 1 except that EMA was vacuum dried for hours at 120° C. to make sure that the polymer was free of any hydrolysis products. The procedure described in Example 3 was used to prepare plates with these polymers. The immobilization of streptavidin was performed at 50 μg/ml without monitoring (off-line immobilization). Small molecule binding capacities were evaluated using 75 μl of 200 nM fluorescein-biotin in 1×PBS added into the wells previously filled with 75 μl of 1×PBS in order to obtain a final concentration of 100 nM fluorescein biotin. The binding signal was recorded over 10 minutes under mixing followed by 2 minutes with no mixing. FIG. 9 shows binding curves for each degree of pre-blocking obtained for the fl-biotin assay after the reference wells have been subtracted out.

Example 12

Preparation of Pre-Blocked Ethylene-Alt-Maleic Anhydride Copolymers with Methoxyethylamine and Corning Epic™ System (Binding of fl-Biotin to Immobilized Streptavidin) Assay Performed on Corning Epic™ Microplate

Figure 10:
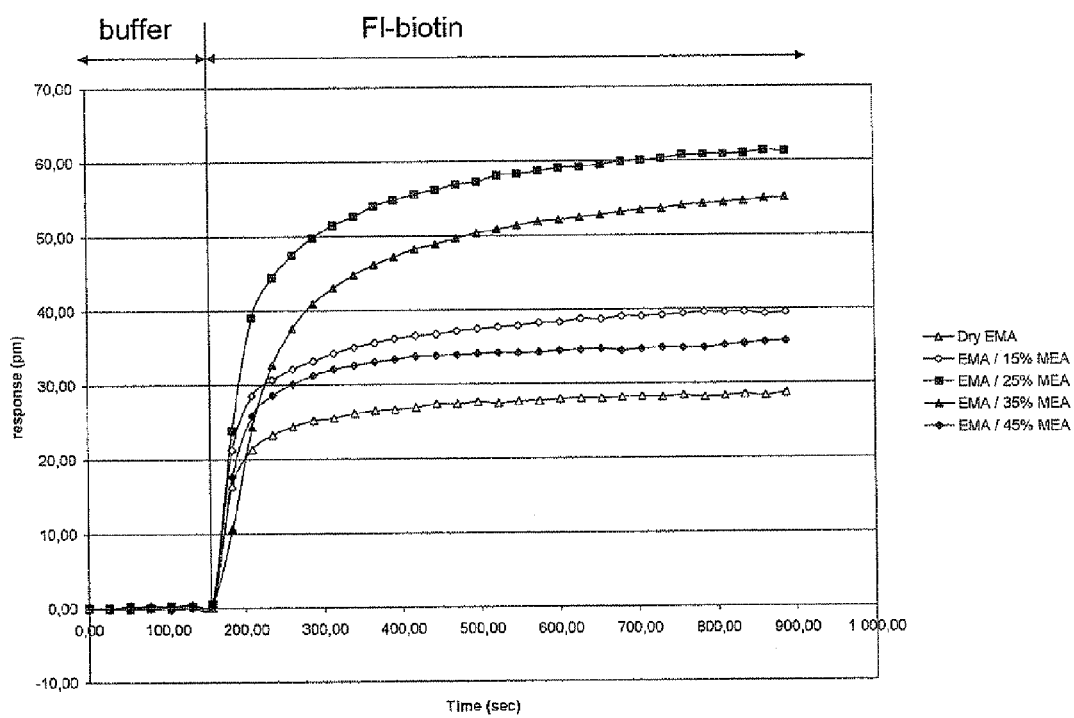
FIG. 10 shows binding curves from the Corning Epic™ System for the fl-biotin assay with plate coated with maleic anhydride copolymers pre-blocked with methoxyethylamine at different pre-blocking degrees.

The procedure of Example 11 was reproduced except that methoxyethyl amine was used instead of ethanolamine. FIG. 10 shows binding curves for each pre-blocking degree obtained for the fl-biotin assay after the reference wells have been subtracted out.

Example 13

This example describes the utility of the present invention for the immobilization of different proteins. Corning 96-well Epic™ plates were coated with either EMA or EMA pre-blocked with 35 mol % of methoxyethylamine (EMA/MEA). Human serum albumin (HSA), immunoglobulin (IgG), chymotrypsinogen, and lysozyme were immobilized in the multiple wells within each plate, and the amount of immobilization was monitored in the Epic™ instrument. The pH for immobilization was 5.5, 6.5, 8.5, and 9.2 for HSA, IgG, chymotrypsinogen, and lysozyme, respectively. As shown in the table below, higher levels of immobilization were observed on EMA/MEA relative to EMA for each protein. The gain in immobilization varied from 28% for chymotrypsinogen to 175% for HSA. These data demonstrate that the present invention is applicable to a variety of biomolecules.

|  | Signal (pm) | SD | % CV | Gain |
|---|---|---|---|---|
| HSA on EMA | 817 | 52 | 6 | — |
| HSA on EMA/MEA | 2244 | 163 | 7 | 2.75 |
| IgG on EMA | 2082 | 62 | 3 | — |
| IgG on EMA | 4480 | 269 | 6 | 2.15 |
| Chymotrypsinogen on EMA | 1584 | 73 | 5 | — |
| Chymotrypsinogen on EMA/MEA | 2027 | 101 | 5 | 1.28 |
| Lysozyme on EMA | 1759 | 88 | 5 | — |
| Lysozyme on EMA/MEA | 2487 | 87 | 4 | 1.41 |

Throughout this application, various publications are referenced. The disclosures of these publications in their entireties are hereby incorporated by reference into this application in order to more fully describe the compounds, compositions and methods described herein.

Various modifications and variations can be made to the materials, methods, and articles described herein. Other aspects of the materials, methods, and articles described herein will be apparent from consideration of the specification and practice of the materials, methods, and articles disclosed herein. It is intended that the specification and examples be considered as exemplary.

What is claimed:

1. A method for making a support for performing an assay, comprising:
pre-blocking a binding polymer to provide a pre-blocked binding polymer of formula (I);
attaching the pre-blocked binding polymer of the formula (I) directly or indirectly to a substrate;

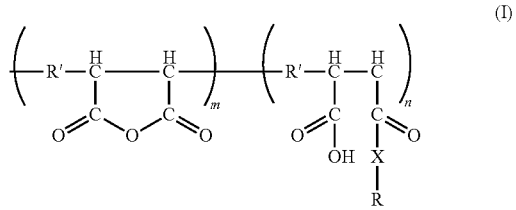

the polymer having a plurality of maleic anhydride reactive groups (m) for attaching a biomolecule and a plurality of inactive groups (n), where
X is a divalent NH, O, or S;
R is H, or a substituted or an unsubstituted, linear or branched, alkyl group, an oligo(ethylene oxide), an oligo(ethylene glycol), or a dialkyl amine;
R' is a residue of a first unsaturated monomer that has been copolymerized with maleic anhydride;
the relative ratio (m:n) of the maleic anhydride reactive groups to the inactive groups is from 0.5 to 10 in the attached pre-blocked binding polymer, and the attached pre-blocked binding polymer does not contain a photoreactive group.

2. The method of claim 1, wherein the pre-blocking is accomplished with a nucleophilic group.

3. The method of claim 1, wherein the pre-blocking is accomplished with an alkyl amine, an alkylhydroxy amine, an alkoxyalkyl amine, an alcohol, an alkyl thiol, water, or $H_2S$.

4. The method of claim 1, wherein the pre-blocking is accomplished with water, ammonia, 2-(2-aminoethoxy)ethanol, N,N-dimethyl ethylenediamine, ethanolamine, ethylenediamine, hydroxyl amine, methoxyethyl amine, ethyl amine, isopropyl amine, butyl amine, propyl amine, hexyl amine, 2-amino-2-methyl-1-propanol, 2-(2-aminoethyl amino)ethanol, 2-(2-aminoethoxy)ethanol, dimethylethanolamine, dibutyl ethanolamine, 1-amino-2-propanol, polyethylene glycol, polypropylene glycol, 4,7,10-trioxa-1,13-tridecanediamine, polyethylene glycol or an amine-terminated-polyethylene glycol, Trizma hydrochloride, or any combination thereof.

5. The method of claim 1, wherein the pre-blocking is accomplished with methoxyethyl amine.

6. The method of claim 1, wherein the substrate comprises a plastic, a polymeric or co-polymeric substance, a ceramic, a glass, a metal, a crystalline material, a noble or semi-noble metal, a metallic or non-metallic oxide, an inorganic oxide, an inorganic nitride, a transition metal, or any combination thereof.

7. The method of claim 1, wherein the substrate comprises gold.

8. The method of claim 1, wherein the substrate comprises $SiO_2$ with a layer comprising $Ta_2O_5$, $Nb_2O_5$, $TiO_2$, $Al_2O_3$, silicon nitride or a mixture thereof, wherein the layer is adjacent to the surface of the $SiO_2$.

9. The method of claim 1, wherein the binding polymer comprises poly(vinyl acetate-maleic anhydride), polystyrene-co-maleic anhydride), poly(isobutylene-alt-maleic anhydride), poly(maleic anhydride-alt-1-octadecene), poly (maleic anhydride-alt-1-tetradecene), poly(maleic anhydride-alt-methyl vinyl ether), poly(triethyleneglycol methylvinyl ether-co-maleic anhydride), or any combination thereof.

10. The method of claim 1, wherein the binding polymer comprises poly(ethylene-alt-maleic anhydride).

11. The method of claim 1, wherein the ratio of reactive groups to inactive groups is from 0.5 to 5.0.

12. The method of claim 1, wherein the ratio of reactive groups to inactive groups is from 0.67 to 3.0.

13. The method of claim 1, wherein the substrate comprises a gold chip, the binding polymer comprises poly(ethylene-alt-maleic anhydride) indirectly attached to the substrate by an aminothiol, and the ratio of reactive groups to inactive groups in the binding polymer is from 0.67 to 3.0.

14. The method of claim 13, wherein prior to attachment to the substrate, the binding polymer is pre-blocked with methoxyethyl amine.

15. The method of claim 1, wherein the substrate comprises a glass substrate with a layer comprising $Ta_2O_5$, $Nb_2O_5$, $TiO_2$, $Al_2O_3$, silicon nitride, $SiO_2$ or a mixture thereof, the binding polymer comprises poly(ethylene-alt-maleic anhydride) indirectly attached to the substrate by a tie layer, wherein the tie layer is derived from aminopropylsilane, and the ratio of reactive groups to inactive groups in the binding polymer is from 0.67 to 3.0.

16. The method of claim 15, wherein prior to attachment to the substrate, the binding polymer is pre-blocked with methoxyethyl amine.

17. A method for making a support for performing an assay, comprising:
attaching a pre-blocked binding polymer of the formula (I) directly or indirectly to a substrate;

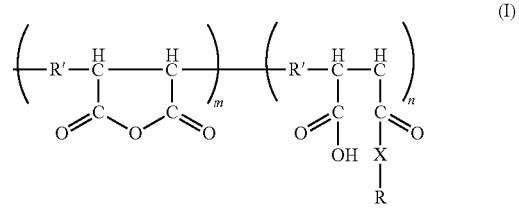

the polymer having a plurality of maleic anhydride reactive groups (m) for attaching a biomolecule and a plurality of inactive groups (n), where
X is a divalent NH, O, or S;
R is H, or a substituted or an unsubstituted, linear or branched, alkyl group, an oligo(ethylene oxide), an oligo(ethylene glycol), or a dialkyl amine;
R' is a residue of a first unsaturated monomer that has been copolymerized with maleic anhydride; and
the ratio of reactive groups to inactive groups is from 0.5 to 10.0 in the attached pre-blocked binding polymer.

18. A support made by the method of claim 1.

19. A support made by the method of claim 17.

20. The support of claim 18 wherein the substrate comprises a cell culture surface.

21. The support of claim 18 wherein the assay comprises a cell based assay.

22. The support of claim 18 wherein the biomolecule comprises a cell.

* * * * *